(12) United States Patent
Shah et al.

(10) Patent No.: US 9,301,884 B2
(45) Date of Patent: Apr. 5, 2016

(54) LIQUID DETECTION SYSTEM HAVING A SIGNALING DEVICE AND AN ABSORBENT ARTICLE WITH GRAPHICS

(71) Applicant: Kimberly-Clark Worldwide, Inc., Neenah, WI (US)

(72) Inventors: Gopal Manoj Shah, Greenville, WI (US); Davis Dang Hoang Nhan, Appleton, WI (US); Sudhanshu Gakhar, Atlanta, GA (US); Stacy Averic Mundschau, Weyauwega, WI (US)

(73) Assignee: KIMBERLY-CLARK WORLDWIDE, INC., Neenah, WI (US)

( * ) Notice: Subject to any disclaimer, the term of this patent is extended or adjusted under 35 U.S.C. 154(b) by 266 days.

(21) Appl. No.: 13/705,368

(22) Filed: Dec. 5, 2012

(65) Prior Publication Data

US 2014/0155850 A1 Jun. 5, 2014

(51) Int. Cl.
*A61F 13/15* (2006.01)
*A61F 13/20* (2006.01)
*A61F 13/42* (2006.01)

(52) U.S. Cl.
CPC ..................... *A61F 13/42* (2013.01)

(58) Field of Classification Search
CPC .............. A61F 13/42; A61F 13/51496; A61F 2013/8497
USPC ........................................................ 604/361
See application file for complete search history.

(56) References Cited

U.S. PATENT DOCUMENTS

| | | | |
|---|---|---|---|
| 4,100,324 A | 7/1978 | Anderson et al. |
| 4,896,600 A | 1/1990 | Rogge et al. |
| 4,940,464 A | 7/1990 | Van Gompel et al. |
| 5,114,781 A | 5/1992 | Morman |
| 5,116,662 A | 5/1992 | Morman |
| 5,284,703 A | 2/1994 | Everhart et al. |
| 5,350,624 A | 9/1994 | Georger et al. |
| 5,458,590 A | 10/1995 | Schleinz et al. |
| 5,486,166 A | 1/1996 | Bishop et al. |
| 5,490,846 A | 2/1996 | Ellis et al. |

(Continued)

FOREIGN PATENT DOCUMENTS

| | | |
|---|---|---|
| EP | 2272475 A1 | 1/2011 |
| JP | 4256436 A | 9/1992 |

(Continued)

OTHER PUBLICATIONS

International Search Report and Written Opinion for PCT/IB2013/059843 dated Feb. 11, 2014; 13 pages.

*Primary Examiner* — Jason Flick
*Assistant Examiner* — Aundria Hairell
(74) *Attorney, Agent, or Firm* — Armstrong Teasdale LLP

(57) ABSTRACT

A liquid detection system includes an absorbent article for personal wear having a liquid permeable liner, an outer cover, and an absorbent body disposed between the liner and the outer cover. The article also includes at least one graphic element, a conductive pattern at least partially superposed with the graphic element, and a barrier layer disposed between the graphic element and the conductive pattern. A non-invasive signaling device is selectively attachable to the outer cover of the absorbent article in overlying relationship with the conductive pattern. The signaling device is adapted to detect the presence of liquid within the absorbent article.

17 Claims, 5 Drawing Sheets

(56) References Cited

U.S. PATENT DOCUMENTS

| | | |
|---|---|---|
| 5,566,616 A | 10/1996 | Schleinz et al. |
| 5,645,542 A | 7/1997 | Anjur et al. |
| 5,766,389 A | 6/1998 | Brandon et al. |
| 5,820,973 A | 10/1998 | Dodge, III et al. |
| 5,883,028 A | 3/1999 | Morman et al. |
| 5,964,743 A | 10/1999 | Abuto et al. |
| 6,200,250 B1 | 3/2001 | Janszen |
| 6,231,557 B1 | 5/2001 | Krautkramer |
| 6,297,424 B1 | 10/2001 | Olson et al. |
| 6,307,119 B1 | 10/2001 | Cammarota et al. |
| 6,362,389 B1 | 3/2002 | Mcdowall et al. |
| 6,552,245 B1 | 4/2003 | Roessler et al. |
| 6,645,190 B1 | 11/2003 | Olson et al. |
| 6,969,378 B1 | 11/2005 | Vukos et al. |
| 7,394,391 B2 | 7/2008 | Long |
| 7,477,156 B2 | 1/2009 | Long et al. |
| 7,655,829 B2 | 2/2010 | Macdonald et al. |
| 8,207,394 B2 | 6/2012 | Feldkamp et al. |
| 8,274,393 B2 | 9/2012 | Ales et al. |
| 2002/0007162 A1* | 1/2002 | Cammarota et al. .......... 604/361 |
| 2002/0110689 A1 | 8/2002 | Hu et al. |
| 2003/0019374 A1 | 1/2003 | Harte |
| 2004/0121681 A1 | 6/2004 | Lindsay et al. |
| 2004/0122386 A1 | 6/2004 | Mocadlo |
| 2004/0122398 A1* | 6/2004 | Schnabel et al. .......... 604/385.01 |
| 2006/0137568 A1 | 6/2006 | Macdonald et al. |
| 2006/0142709 A1 | 6/2006 | Quincy, III |
| 2007/0142797 A1 | 6/2007 | Long et al. |
| 2009/0005748 A1* | 1/2009 | Ales et al. ..................... 604/361 |
| 2009/0326417 A1* | 12/2009 | Ales et al. ..................... 600/584 |
| 2010/0168694 A1 | 7/2010 | Gakhar et al. |
| 2010/0168702 A1 | 7/2010 | Ales, III et al. |
| 2011/0040267 A1* | 2/2011 | Wada et al. .................... 604/318 |
| 2012/0116337 A1 | 5/2012 | Ales et al. |
| 2012/0179125 A1 | 7/2012 | Kanya et al. |
| 2012/0206265 A1 | 8/2012 | Solazzo et al. |

FOREIGN PATENT DOCUMENTS

| | | |
|---|---|---|
| JP | 2005263610 A | 9/2005 |
| WO | 9112030 A1 | 8/1991 |
| WO | 0037009 A2 | 6/2000 |
| WO | 03051254 A2 | 6/2003 |

* cited by examiner

LIQUID DETECTION SYSTEM HAVING A SIGNALING DEVICE AND AN ABSORBENT ARTICLE WITH GRAPHICS

FIELD

The field of the present invention relates generally to absorbent articles intended for personal wear, and more particularly to absorbent articles having graphics and a detection system for detecting when a bodily fluid is present in the article (e.g., when a wearer urinates into the absorbent article).

BACKGROUND

Disposable absorbent articles find widespread use as personal care products such as diapers, children's toilet training pants and other infant and child care products, adult incontinence garments and other adult care products, sanitary napkins and other feminine care products and the like, as well as surgical bandages and sponges. These articles absorb and contain body waste and are intended to be discarded after a limited period of use, i.e., the articles are not intended to be laundered or otherwise restored for reuse. Conventional disposable absorbent articles comprise an absorbent body disposed between an inner layer adapted for facing and typically contacting the wearer's skin and an outer layer for inhibiting liquid waste absorbed by the absorbent body from leaking out of the article. The inner layer of the absorbent article is typically liquid permeable to permit body waste to pass therethrough for absorption by the absorbent body.

Disposable absorbent training pants, in particular, are useful in toilet training children. Typically, these training pants are similar to washable, cloth underwear in the manner in which they are put on and worn, yet provide an absorbent function similar to conventional diapers. Training pants are designed to provide a child undergoing toilet training with a garment that eases the transition from diapers to washable, cloth underwear as they become more confident in their ability to use the toilet independently. Indeed, one important aspect of the total toilet training process is the change from diapers to training pants to help the child understand that he or she should now use the toilet. Although the use of training pants and positive encouragement from the caregiver has been helpful in the toilet training process, there is still much room for improvement.

One motivational mechanism used to encourage such a transition is the use of disposable training pants that more closely resemble an actual pair of underwear. Specifically, a child is encouraged to wear a garment that resembles underwear worn by older children. To mimic the appearance of underwear and raise the interest of a child during toilet training, training pants are known to have graphics that are visible from outside the pants, such as by being applied to their exterior or outer surface. The graphics may be in the form of a character, object and/or alphanumeric (e.g., numbers, words, phrases, instructions, etc.). Graphics applied to such disposable articles may also provide visual assistance to the wearer or to the caregiver securing the article on the wearer.

Another motivational mechanism used to encourage or facilitate a child's transition to regular underwear is the use of wetness indicators, which are devices design to indicate to the wearer and/or caregiver when a bodily fluid has been released into the article (e.g., when a wearer urinates into the absorbent article). Various types of moisture or wetness indicators have been used in absorbent articles. Known wetness indicators include various passive indicators such as indicator strips, printing, or other devices secured or otherwise formed within each absorbent article. Some wetness indicators include suitable alarm devices that are designed to send a signal when the wetness indicator senses moisture or wetness. The alarm devices can produce an audible, tactile, electromagnetic, or visual signal.

In some embodiments, inexpensive conductive threads, foils, or paper have been placed in absorbent articles with wetness indicators. The conductive materials serve as conductive leads for a signaling device and form an open circuit in the article that can be closed when a fluid, such as urine, closes the circuit. In these embodiments, although the absorbent articles having the conductive threads, foils, or paper therein are disposable, the signaling devices are typically not. Thus, the signaling devices are intended to be removed from a used article and reattached to a subsequent, new article.

Several technologies have enabled wetness detection with little to no product alteration using non-invasive sensors that can be removably placed on the absorbent article. By way of example, U.S. Patent Application Publication No. 2010/0168694, which is incorporated herein by reference, discloses an infrared wetness detection system for an absorbent article that includes a non-invasive sensor that measures infrared reflectance at some depth within the absorbent article. U.S. Pat. No. 8,274,393, which is incorporated herein by references, discloses the use of various sensors, such as a temperature sensor, a conductivity sensor, a humidity sensor, a chemical sensor, a vibration sensor, or a material expansion sensor placed on an outside cover of an absorbent article. U.S. Pat. No. 8,207,394, which is incorporated by reference herein, discloses the use of an induction coil sensor for wetness detection in an absorbent article. U.S. Patent Application Publication No. 2010/0168702, which is incorporated herein by reference, discloses a non-invasive capacitive sensor system and associated circuitry for wetness detection.

While a non-invasive signaling device provides many advantages, problems can be encountered in properly associating a particular signaling device with a proprietary product. In particular, due to the non-invasive nature of such signaling devices, a proprietary signaling device can be used with any absorbent article, regardless of the manufacturer or source of the absorbent article. Moreover, non-invasive signaling devices can be used on products that have not been safety cleared for use with a signaling device.

U.S. Patent Application Publication No. 2012/0116337, which is incorporated herein by reference, discloses a non-invasive signaling device capable of detecting the presence of one or more identifiable characteristics on the absorbent article. In particular, the absorbent article can be manufactured with a particular identifiable characteristic that can be sensed or detected by the non-invasive signaling device. When the non-invasive signaling device detects the presence of the identifiable characteristic on the absorbent article, the non-invasive signaling device is permitted to operate to detect the presence of fluid in the absorbent article. If the signaling device is used on an absorbent article that does not include the identifiable characteristic, the non-invasive signal will not operate, thereby preventing the use of a proprietary signaling device on an unauthorized product.

In one embodiment disclosed in U.S. Patent Application Publication No. 2012/0116337, the identifiable characteristic is a predefined color. In another disclosed embodiment, the identifiable characteristic is a conductive pattern printed on the absorbent article. If the predefined color or the electrical characteristics of the printed conductive pattern falls within a predefined range, the signaling device will be permitted to operate. However, one potential issue with both of these embodiments is that the predefined color and the printed conductive pattern are readily visible exterior the absorbent article. As a result, the predefined color or printed conductive pattern potentially diminishes the visual quality of any graphics printed on the exterior of or otherwise visible exterior the absorbent article.

In view of the above, a need currently exists for an absorbent article having one or more identifiable characteristics that are detectable by a non-invasive signaling device and that do not diminishes the visual quality of any graphics printed on the exterior of or otherwise visible exterior the absorbent article.

BRIEF DESCRIPTION

In one aspect, a liquid detection system generally comprises an absorbent article for personal wear comprising a liquid permeable liner, an outer cover, and an absorbent body disposed between the liner and the outer cover. The article also comprises at least one graphic element, a conductive pattern at least partially superposed with the graphic element, and a barrier layer disposed between the graphic element and the conductive pattern. A non-invasive signaling device is selectively attachable to the outer cover of the absorbent article in overlying relationship with the conductive pattern. The signaling device is adapted to detect the presence of liquid within the absorbent article.

In another aspect, an absorbent article for use with a non-invasive signaling device generally comprises a liquid permeable liner, an outer cover, and an absorbent body disposed between the liner and the outer cover. The article also comprises at least one graphic element, a conductive pattern at least partially superposed with the graphic element, and a barrier layer disposed between the graphic element and the conductive pattern.

In yet another aspect, an outer cover for an absorbent article generally comprises at least one graphic element, a conductive pattern at least partially superposed with the graphic element, and a barrier layer disposed between the graphic element and the conductive pattern.

DETAILED DESCRIPTION OF THE DRAWINGS

Figure 1:
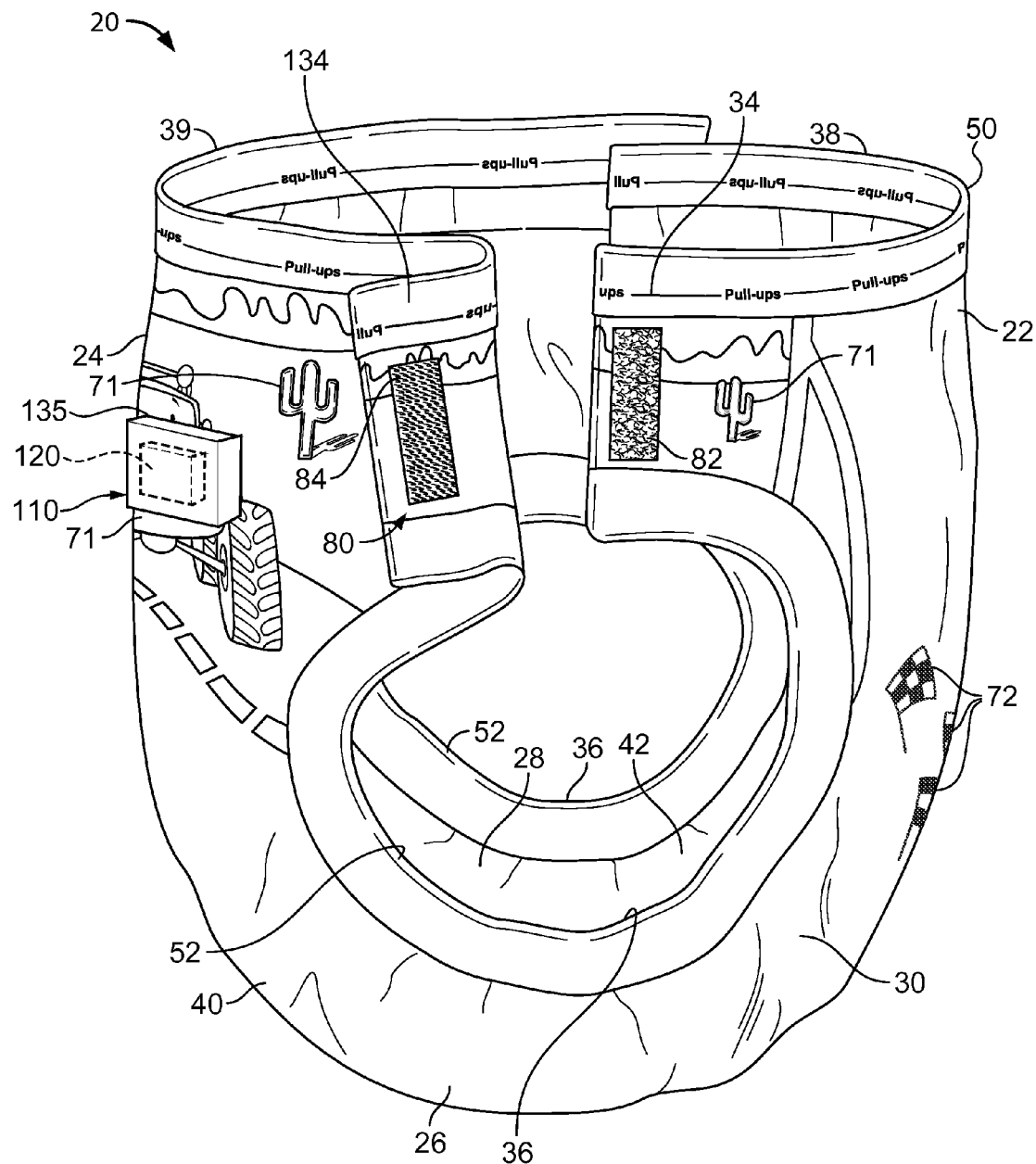
FIG. 1 is a side perspective of an embodiment of an article in the form of a pair of training pants having a mechanical fastening system illustrated in a fastened condition on one side of the training pants and in an unfastened condition on the opposite side thereof.

Referring now to the drawings and in particular to FIG. 1, an absorbent article according to one embodiment is representatively illustrated therein in the form of children's toilet training pants and is indicated in its entirety by the reference numeral 20. The pair of training pants 20 illustrated in FIG. 1 is shown in a partially fastened condition. It is understood that the absorbent article may or may not be disposable. Disposable articles refer to articles that are intended to be discarded after a limited period of use instead of being laundered or otherwise conditioned for reuse. It is also understood that the present invention is suitable for use with various other absorbent articles, including, but not limited to, diapers, feminine hygiene products, incontinence products, medical garments, surgical pads and bandages, other personal care or health care garments, and the like.

By way of illustration only, various materials and methods for constructing training pants such as the pants 20 of the various aspects of the embodiments described herein are disclosed in PCT Patent Application WO 00/37009 published Jun. 29, 2000 by A. Fletcher et al; U.S. Pat. No. 4,940,464 issued Jul. 10, 1990 to Van Gompel et al.; U.S. Pat. No. 5,766,389 issued Jun. 16, 1998 to Brandon et al.; and U.S. Pat. No. 6,645,190 issued Nov. 11, 2003 to Olson et al., which are all incorporated herein by reference.

Figure 2:
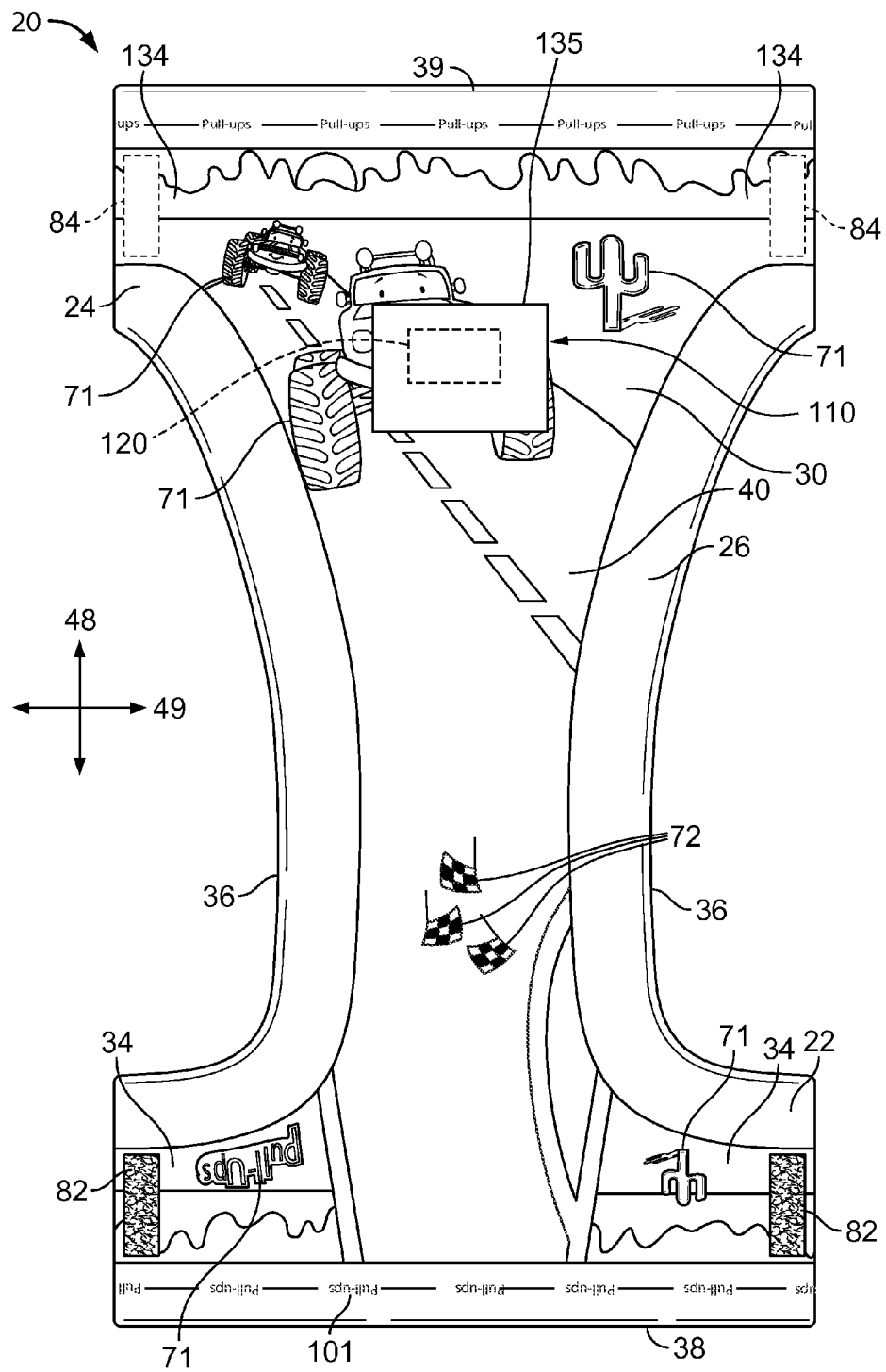
FIG. 2 is a plan view of the training pants of FIG. 1 with the pants in an unfastened, unfolded and laid flat condition, and showing an outer surface of the training pants, which is the surface of the training pants that faces away from the wearer.
Figure 3:
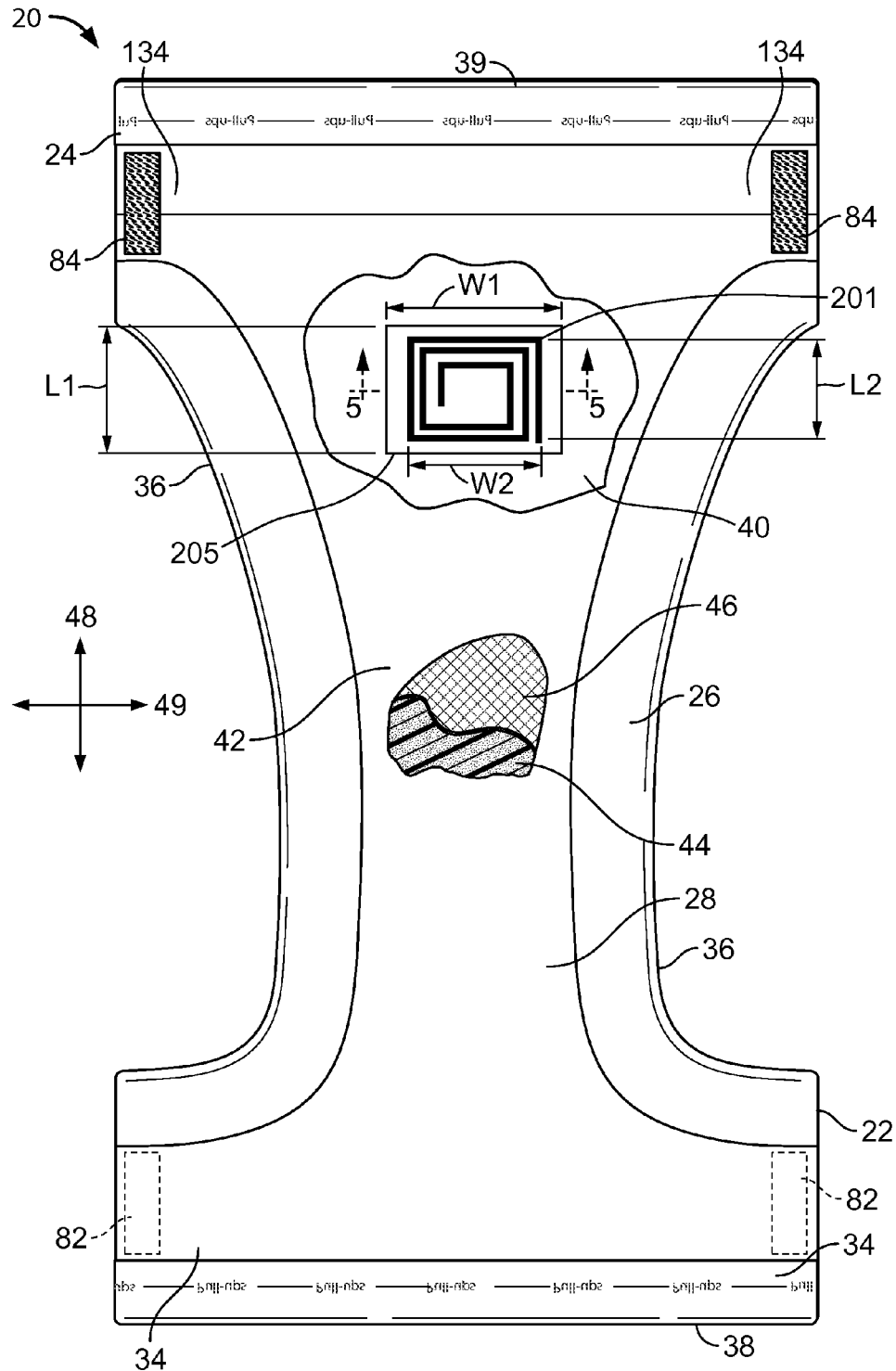
FIG. 3 is a plan view similar to FIG. 2 but showing an inner surface of the training pants, which is the surface of the training pants that faces the wearer when worn and with portions cut away to show underlying features.

As seen in FIGS. 2 and 3, the pants 20 define a longitudinal direction 48 and a lateral direction 49 perpendicular to the longitudinal direction. The pants 20 include a pair of longitudinal end regions, otherwise referred to herein as a front waist region 22 and a back waist region 24, and a center region, otherwise referred to herein as a crotch region 26, extending longitudinally between and interconnecting the front and back waist regions 22, 24. The front and back waist regions 22, 24 include those portions of the pants 20, which when worn, wholly or partially cover or encircle the waist or mid-lower torso of the wearer. The crotch region 26 generally is that portion of the pants 20 which, when worn, is positioned between the legs of the wearer and covers the lower torso and crotch of the wearer. The pants 20 also define an inner surface 28 adapted in use (e.g., positioned relative to the other components of the pants 20) to face and be disposed toward the wearer, and an outer surface 30 opposed with the inner surface for facing away from the wearer.

As used herein, the terms inner and outer are used in reference to a direction taken perpendicular to the longitudinal and lateral directions of the pants 20 (i.e., the absorbent article), with the term inner being used to indicate a direction nearer to a wearer of the article and the term outer indicating a direction away from the wearer.

With additional reference to FIGS. 2 and 3, the pair of training pants 20 has a pair of laterally opposite side edges 36 and a pair of longitudinally opposite waist edges (broadly, longitudinal ends), respectively designated front waist edge 38 and back waist edge 39. Front and back side panels 34, 134 of the pants, upon wearing thereof, include the portions of the training pants 20 which are positioned on the hips of the wearer. These front and back side panels 34, 134 can be permanently bonded together to form the three-dimensional configuration of the pants 20, or be releasably connected with one another such as by the fastening system 80 as illustrated in FIG. 1. The side panels 34, 134 may be formed integrally with the rest of the training pants, or be formed separate therefrom and secured thereto by suitable bonding techniques, such as adhesive bonding, pressure bonding, thermal bonding and/or ultrasonic bonding.

The illustrated training pants 20 have an outer cover 40 (broadly, an outer layer or substrate of the pants) having an outer surface at least in part and in the illustrated embodiment entirely defining the outer surface 30 of the training pants. As seen in FIGS. 1 and 3, a bodyside liner 42 (broadly, an inner layer or substrate of the pants), having an inner surface at least in part and in the illustrated embodiment entirely defining the inner surface 28 of the pants, is in overlaid or opposed relationship with the outer cover 40. The liner 42 can be suitably joined to the outer cover 40 along at least a portion of the longitudinal ends 38, 39 of the pants 20 and/or along the side edges 36 thereof by any suitable means such as, without limitation, adhesive bonding, ultrasonic bonding, thermal bonding, and the like. An absorbent structure 44 (FIG. 3) is disposed between the outer cover 40 and the bodyside liner 42 for absorbing liquid body exudates exuded by the wearer.

With the training pants 20 in a fastened position as partially illustrated in FIG. 1, the front and back waist regions 22, 24 are connected together by the fastening system 80 to define the three-dimensional pants configuration having a waist opening 50 and a pair of leg openings 52. The front and back waist edges 38, 39 (e.g., longitudinal ends) of the training pants 20 are configured to encircle the waist of the wearer to define the waist opening 50 (FIG. 1) of the pants.

The illustrated fastening system 80 includes laterally opposite first fastening components 82 adapted for refastenable engagement to corresponding laterally opposite second fastening components 84. In one aspect, a surface of each of the fastening components 82, 84 includes a plurality of engaging elements. The engaging elements of the first fastening components 82 are adapted to repeatedly engage and disengage corresponding engaging elements of the second fastening components 84 to releasably secure the pants 20 in its three-dimensional configuration. The fastening components 82, 84 can include any refastenable fasteners suitable for absorbent articles, such as adhesive fasteners, cohesive fasteners, mechanical fasteners, or the like. Suitable fastening systems are also disclosed in the previously incorporated PCT Patent Application WO 00/37009 published Jun. 29, 2000 by A. Fletcher et al. and the previously incorporated U.S. Pat. No. 6,645,190 issued Nov. 11, 2003 to Olson et al.

The outer cover 40 suitably comprises a material layer that is substantially liquid impermeable. For example, the outer cover 40 may comprise a single layer of liquid impermeable material, or more suitably a multi-layered laminate structure in which at least one of the layers is liquid impermeable. For instance, the outer cover 40 can comprise a liquid permeable outer layer and a liquid impermeable inner layer that are suitably joined together by a laminate adhesive, ultrasonic bonds, thermal bonds, pressure bonds or the like. The outer layer may also be made of those materials of which the liquid permeable bodyside liner 42 is made. While it is not a necessity for the outer layer to be liquid permeable, it is suitable that it provides a relatively cloth-like texture to the wearer.

The inner layer of the outer cover 40 can be both liquid and vapor impermeable, or it may be liquid impermeable and vapor permeable. The inner layer can be manufactured from a thin plastic film, although other flexible liquid impermeable materials may also be used. The inner layer, or the liquid impermeable outer cover 40 when a single layer, prevents waste material from wetting articles, such as bed sheets and clothing, as well as the wearer and caregiver.

Alternatively, the outer cover 40 may include a woven or non-woven fibrous web layer that has been totally or partially constructed or treated to impart the desired levels of liquid impermeability to selected regions that are adjacent or proximate the absorbent structure. The outer cover 40 may also be stretchable, and in some aspects it may be elastomeric. Reference is made to U.S. Pat. No. 5,883,028, issued to Morman et al., U.S. Pat. No. 5,116,662 issued to Morman and U.S. Pat. No. 5,114,781 issued to Morman, all of which are hereby incorporated herein by reference, for additional examples of suitable outer cover 40 materials.

The bodyside liner 42 is suitably compliant, soft-feeling, and non-irritating to the wearer's skin. The bodyside liner 42 is also sufficiently liquid permeable to permit liquid body exudates to readily penetrate through its thickness to the absorbent structure 44. As an example, one suitable liquid permeable bodyside liner 42 is a nonwoven polyethylene/polypropylene bicomponent web having a basis weight of about 27 gsm; the web may be spunbonded or a bonded carded web. Alternatively, the bodyside liner 42 may be stretchable, and in some aspects it may be elastomeric. Reference is made to U.S. patent application Ser. No. 09/563,417 filed on May 3, 2000 by Roessler et al., U.S. patent application Ser. No. 09/698,512 filed on Oct. 27, 2000 by Vukos et al., both of which are incorporated by reference herein, for additional information regarding suitable bodyside liner materials.

The absorbent structure 44 is disposed between the outer cover 40 and the bodyside liner 42. The absorbent structure 44 in one suitable embodiment extends longitudinally from the crotch region 26 into both the front and back waist regions 22, 24. It is contemplated, however, that the absorbent structure 44 may extend from the crotch region 26 into only the front waist region 22, or only the back waist region 24, without departing from the scope of this invention.

The absorbent structure 44 can be suitably compressible, conformable, non-irritating to a wearer's skin, and capable of absorbing and retaining liquids and certain body wastes. For example, the absorbent structure 44 may include cellulosic fibers (e.g., wood pulp fibers), other natural fibers, synthetic fibers, woven or nonwoven sheets, scrim netting or other stabilizing structures, superabsorbent material, binder materials, surfactants, selected hydrophobic materials, pigments, lotions, odor control agents or the like, as well as combinations thereof.

The materials may be formed into an absorbent web structure by employing various conventional methods and techniques known in the art. For example, the absorbent structure 44 may be formed by a dry-forming technique, an air forming technique, a wet-forming technique, a foam-forming technique, or the like, as well as combinations thereof. Methods and apparatus for carrying out such techniques are well known in the art. The absorbent structure 44 may alternatively include a coform material such as the material disclosed in U.S. Pat. No. 4,100,324 to Anderson, et al.; U.S. Pat. No. 5,284,703 to Everhart, et al.; and U.S. Pat. No. 5,350,624 to Georger, et al.; which are incorporated herein by reference.

The term "coform material" generally refers to composite materials comprising a mixture or stabilized matrix of thermoplastic fibers and a second non-thermoplastic material. As an example, coform materials are made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles, inorganic absorbent materials, treated polymeric staple fibers and the like. Any of a variety of synthetic polymers may be utilized as the melt-spun component of the coform material. For instance, in certain aspects, thermoplastic polymers can be utilized. Some examples of suitable thermoplastics that can be utilized include polyolefins, such as polyethylene, polypropylene, polybutylene and the like; polyamides; and polyesters. In one aspect, the thermoplastic polymer is polypropylene.

Superabsorbent material may be suitably present in the absorbent structure 44 in an amount of from about 0 to about 90 weight percent based on total weight of the absorbent structure. The absorbent structure 44 may suitably have a density within the range of about 0.10 to about 0.35 grams per cubic centimeter. Superabsorbent materials are well known in the art and can be selected from natural, synthetic, and modified natural polymers and materials.

In one aspect, the absorbent structure 44 may be stretchable so as not to inhibit the stretchability of other components to which the absorbent structure may be adhered, such as the outer cover 40 and bodyside liner 42. For example, the absorbent structure may include materials disclosed in U.S. Pat. Nos. 5,964,743, 5,645,542, 6,231,557, 6,362,389, and international patent application WO 03/051254, the disclosure of each of which is incorporated by reference herein. Optionally, a substantially liquid permeable wrapsheet (not shown) may surround the absorbent structure 44 to help maintain the integrity of the absorbent structure 44.

A surge management layer 46 (FIG. 3) may be disposed between the absorbent structure 44 and the liner 42, and may or may not be attached to various components of the pair of training pants 20 such as the absorbent structure and/or the bodyside liner 42. A surge management layer 46 helps to decelerate and diffuse surges or gushes of liquid that may be rapidly introduced into the absorbent structure 44 of the pair of training pants 20. Desirably, the surge management layer 46 can rapidly accept and temporarily hold the liquid prior to releasing the liquid into the storage or retention portions of the absorbent structure 44. Examples of suitable surge management layers are described in U.S. Pat. No. 5,486,166; and U.S. Pat. No. 5,490,846. Other suitable surge management materials are described in U.S. Pat. No. 5,820,973. The entire disclosures of these patents are incorporated by reference herein. It is understood, however, that the surge management layer 46 may be omitted and remain within the scope of this invention.

As shown in FIGS. 1 and 2, the training pants 20, and in particular the outer cover 40 thereof, has one or more graphic elements 71 (referred to particularly herein as outer graphic elements) applied thereto. Examples of such outer graphic elements 71 include, but are not limited to, scenes, characters, animals, objects, alphanumerics such as numbers, letters, words, phrases and the like, highlighting or emphasizing of leg and waist openings 52, 50 in order to make product shaping more evident or visible to the user; highlighting or emphasizing areas of the product to simulate functional components such as elastic leg bands, elastic waistbands, simulated "fly openings" for boys, ruffles for girls; highlighting areas of the product to change the appearance of the size of the product; registering wetness indicators, temperature indicators, and the like in the product; registering a back label, or a front label, in the product; and registering written instructions at a desired location in the product. The outer graphic elements 71 are suitably positioned on the training pants 20 at predetermined locations, e.g., relative to the longitudinal and lateral directions of the pants 20.

The outer graphic elements 71 may be applied to the pants 20 using a suitable printing process, such as a flexographic printing process. Flexographic printing apparatus and processes are known to those skilled in art and need not be further described herein. For example such apparatus are shown and/or described in U.S. Pat. No. 5,458,590 (Schleinz et al.); U.S. Pat. No. 5,566,616 (Schleinz et al.); U.S. 2003/0019374A1 (Harte); and U.S. Pat. No. 4,896,600 (Rogge et al.). Alternatively, the outer graphic elements 71 may be printed, sprayed, or otherwise applied to the training pants 20 by another suitable printing method (e.g., ink jet, rotogravure, etc.) or by combinations thereof, such as by applying the various graphic elements 71 to the pants 20 in different printing stages.

In the illustrated embodiment of FIGS. 1 and 2, one or more of the outer graphic elements 71 is suitably disposed on the training pants 20 so as to be visible from exterior of the pants thereby resembling a conventional cloth pair of underwear or other garment. The term "visible from exterior of the pants" as used herein means visible while looking at the outer surface 30 of the pants 20 in a direction from the outer surface to the inner surface 28 of the pants. The term "visible" is used here to mean visible to an unaided human eye with 20-20 (natural or corrected) vision from a distance typically incurred during normal use of the pants, such as by the wearer during donning of the pants.

In one particularly suitable embodiment one or more of the outer graphic elements 71 are applied to the outer cover 40, and more suitably to the outer surface of the outer cover (and hence to the outer surface 30 of the training pants 20). It is understood, however, that one or more of the outer graphic elements 71 may be applied other than to the outer facing surface of the outer cover 40, such as to the inner facing surface of the outer cover, or where the outer cover is of multiple layers of material one or more of the outer graphic elements 71 may be applied to the inner and/or outer surface of any one or more of the layers of such an outer cover as described below in more detail.

Each of the outer graphic elements 71 illustrated in FIGS. 1 and 2 are suitably permanent graphics, i.e., applied using a permanent ink. The term "permanent graphic" is used herein to refer to a graphic element that does not substantially change its degree of visibility when the absorbent article is insulted with urine. It is contemplated, however, that one or more of the outer graphic elements 71 may comprise an active graphic for providing a caregiver and/or the wearer of the pair of training pants 20 a signal that a liquid insult has occurred. As used herein, the term "active graphic" refers to a graphic element that visibly changes appearance in response to a liquid insult of the article. For example, such an active graphic may fade or otherwise appear faint following liquid insult (often referred to as a fading graphic), or the active graphic may change from a relatively faint appearance to a bolder, or at least more readily visible appearance (often referred to as an appearing graphic), or the active graphic may change colors in response to a liquid insult.

In the illustrated embodiment of FIGS. 1 and 2, for example, outer graphic elements 72 in the form of checkered flags are suitably active graphics, and more suitably fading graphics. Examples of active graphics suitable for use with the training pants 20 are described in U.S. Pat. No. 6,297,424 issued Oct. 2, 2001 to Olson, et al. and U.S. Pat. No. 6,307,119 issued Oct. 23, 2001 to Cammarota et al., which are incorporated by reference herein.

As seen in FIGS. 1 and 2, the illustrated pair of training pants 20 has a signaling device, indicated generally at 110, releasably attached to the outer surface 30 thereof. Suitable signaling devices can be found, for example, in U.S. Patent Application Publication No. 2010/0168702, entitled "Conductor-Less Detection System For An Absorbent Article", and U.S. Patent Application Publication No. 2010/0168694, entitled "Infrared Wetness Detection System For An Absorbent Article", both of which are hereby incorporated by reference.

The illustrated signaling device 110 includes a non-invasive sensor adapted to detect liquid (e.g., urine) in the training pants 20. In the illustrated embodiment, for example, the non-invasive sensor is a capacitive sensor 120. In other embodiments, any other suitable non-invasive sensor for detecting liquid in the pair of training pants 20 may be used. In one suitable embodiment, the capacitive sensor 120 includes two electrodes creating an electrostatic field that extends beyond the face of the electrodes and, in this case, beyond the face of the signaling device 110. In other embodiments, any other suitable capacitive sensor may be used. In some embodiments capacitive sensor 120 includes an array of capacitive sensors.

In general, substances adjacent the capacitive sensor 120 act as dielectrics for a capacitor. If the substance changes, the dielectric constant and the capacitance change. Conductive substances, such as urine, water, etc., have significantly higher dielectric constants than either air or the pair of training pants 20, and produce a significant change in capacitance when present in the pair of training pants. Thus, by monitoring, directly or indirectly, changes in capacitance, signaling device 110 can detect the presence or absence of liquids in the pair of training pants 20.

In one example embodiment, a charge time measurement unit (CTMU) is used in connection with a microcontroller to directly to detect changes in capacitance as the dielectric changes in presence of wetness. In other methods, wetness is detected by detecting one or more changes to a circuit operation that are caused by the changing dielectric constant and capacitance. For example, changes to the dielectric constant caused by liquid in the pair of training pants 20 will change the resonant frequency of an LC circuit. Changes to the resonant frequency are detected by a frequency-to-voltage (F/V) converting chip and/or a microcontroller and used to determine when liquid is present in the pair of training pants 20. In some embodiments, the response of a resistor-capacitor (RC) circuit is monitored to determine when liquid is present in the pair of training pants 20. A RC circuit has a characteristic discharge curve dependent on the capacitor under test. When the liquid is present in the pair of training pants 20, the changed capacitance produces a different discharge curve. The signaling device 110 compares the discharge curve (or an aspect of the curve) to the known discharge curve of the RC circuit in the absence of liquid to determine when liquid is present in the pair of training pants 20.

The signaling device 110 may use any suitable algorithm to detect wetness in the pair of training pants 20 using the capacitive sensor 120. Two exemplary algorithms that may be used include a sensor-by-sensor detection and compare algorithm, and a coherent addition algorithm.

The signaling device 110 can emit any suitable signal to indicate to the user or care giver that the pair of training pants 20 has been insulted. The signal, for instance, can include an audible signal, a tactile signal, an electromagnetic signal, or a visual signal. The audible signal, for example, can be as simple as a beep or can include a musical tune. In still another aspect, the signaling device can emit a wireless signal that then activates a remote device, such as a cellular telephone.

As illustrated in FIG. 2, the capacitive sensor 120 is disposed within a housing 135 that is adapted to be selectively attached to the pair of training pants 20. The housing 135 can be a pouch or a rigid or semi-rigid housing that attaches to the outer surface 30 of the outer cover 40 of the pair of training pants 20 near the region where insults are expected. Suitable attachment mechanisms include, e.g., adhesive, hook and loop, mechanical fasteners such as snaps, clips, or clasps, any other suitable attachment mechanism, or any combination thereof. Various attachment mechanisms include those disclosed in U.S. Patent Application Publication No. 2007/0142797 to Long, et al. and entitled "Garments With Easy-To-Use Signaling Device"; U.S. Pat. No. 7,394,391 to Long and entitled "Connection Mechanisms in Absorbent Articles for Body Fluid Signaling Devices"; and U.S. Pat. No. 7,477,156 to Long, et al. and entitled "Connection Mechanisms In Absorbent Articles For Body Fluid Signaling Devices", which are incorporated herein by reference.

It is contemplated that the capacitive sensor 120 can be placed in any suitable location on the pair of training pants 20. For instance, the capacitive sensor 120 can be placed in the crotch region 26, on the back region 24, or on the front region 22 of the pair of training pants 20 depending upon various factors. As described herein, the capacitive sensor 120 can suitably be placed on the outer surface 30 of the outer cover 40 of the pair of training pants 20. Suitably, the capacitive sensor 120 is placed on the outer surface 30 of the front region 22 of the pair of training pants 20.

In one suitable embodiment, the signaling device 110 includes one or more sensors that are configured to detect the presence of the one or more identifiable characteristics on the pair of training pants 20. If the one or more identifiable characteristics are detected, the signaling device 110 can be activated such that the sensors of the signaling device can detect the presence of a substance in the pair of training pants 20 and can provide an alert to the user of the pair of training pants. U.S. Patent Application Publication No. 2012/0116337, which is incorporated herein by reference, discloses a non-invasive signaling device capable of detecting the presence of one or more identifiable characteristics on the absorbent article.

Figure 4:
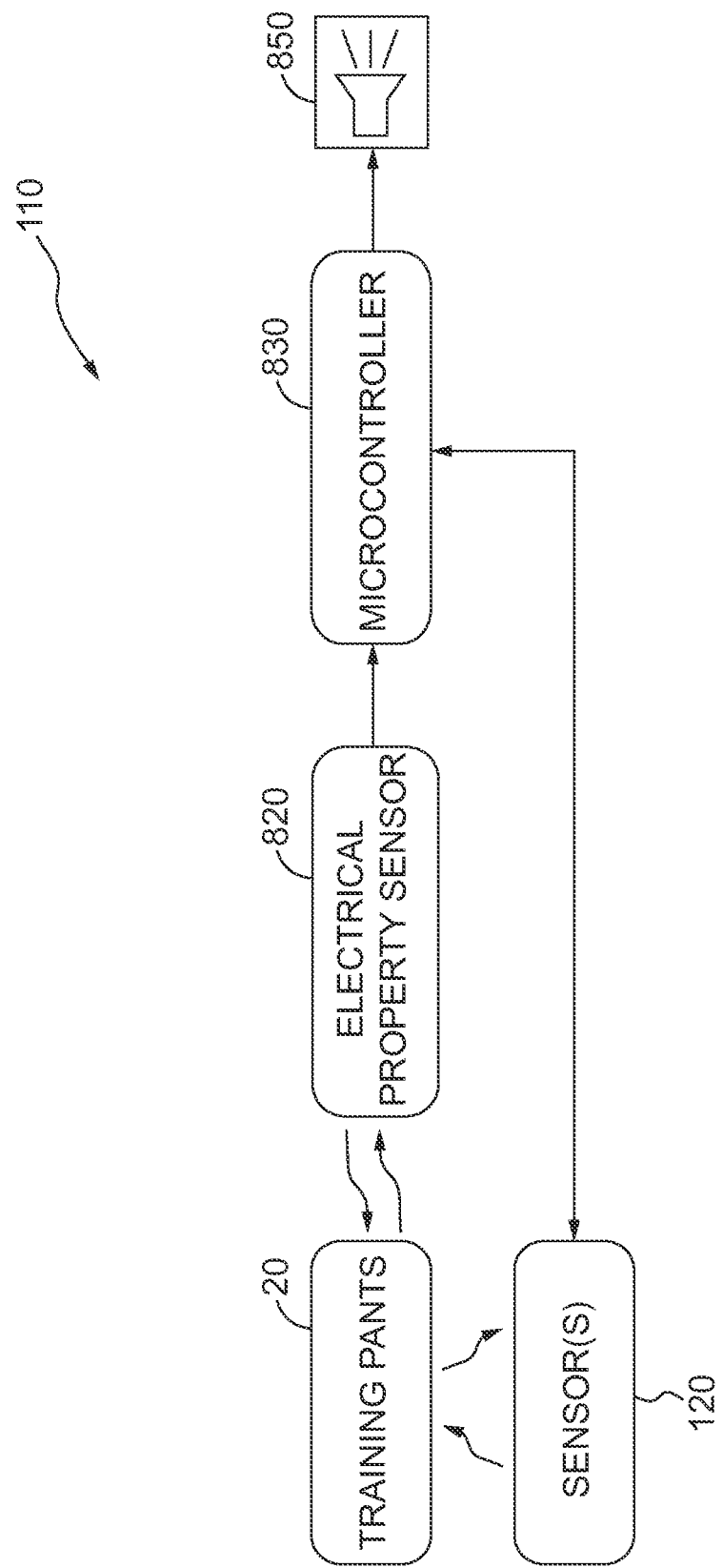
FIG. 4 is a block diagram of an embodiment of a signaling device capable of detecting the presence of one or more identifiable characteristics in the training pants.

FIG. 4 is a block diagram of an exemplary embodiment of the signaling device 110 for detecting the presence of one or more identifiable characteristics in the pair of training pants 20. The signaling device 110 is configured to monitor electrical characteristics, such as capacitance, inductance, and/or conductivity, of conductive patterns printed on the pair of training pants 20. In one suitable embodiment, which is illustrated in FIG. 3, the pair of training pants 20 include a conductive pattern 201 printed on the inner surface (i.e., the surface that faces the wearer during use) of the outer cover 40. If the electrical characteristics of the conductive pattern 201 fall within a predefined range, the signaling device 110 will be permitted to operate.

The conductive pattern 201 illustrated in FIG. 3 has a particular "electrical fingerprint" based on the conductivity, capacitance, and/or inductance of the conductive pattern. The signaling device 110 can use one or more sensors to determine if the particular "electrical fingerprint" is present on the pair of training pants. The presence of the "electrical fingerprint" permits operation of the signaling device 110. If the "electrical fingerprint" of the conductive pattern 201 is not detected by the signaling device 110, the signaling device will not operate.

As illustrated in FIG. 4, the signaling device 110 of the illustrated embodiment includes an electrical property sensor 820, such as a conductivity sensor, capacitive sensor, and/or other sensor or combination of sensors, to detect an electrical characteristic of the conductive pattern 201 printed on the pair of training pants 20. The electrical property sensor 820 can be a part of other non-invasive sensors on the signaling device 110 or can be stand alone. For instance, in a particular embodiment, the non-invasive sensors 120 of signaling device 110 include a plurality of capacitive sensors designed to detect a substance in the pair of training pants 20 as described above. The electrical property sensor 820 can be one of the non-invasive capacitive sensors 120 configured to detect electrical properties of the conductive pattern 201 printed on the pair of training pants 20.

With reference still to FIG. 4, a microcontroller 830 is configured to activate the sensors 120 of signaling device 110 if the electrical characteristics detected from the pair of training pants 20 falls within a predefined range. The microcontroller 830 monitors the electrical characteristics of the conductive pattern 201 on the pair of training pants 20 by analyzing signals received from the electrical property sensor 820. If the electrical characteristics do not fall within the predefined range, the microcontroller 830 does not activate the non-invasive sensors 120 of the signaling device 110 thereby inhibiting the signaling device 110 from being used on an unauthorized product. If the microcontroller 830 determines that the electrical characteristics fall within the predefined range, the microcontroller 830 activates the non-invasive sensors 120 and monitors for the presence of liquid in the pair of training pants 20 as described herein. In one suitable embodiment, the microcontroller 830 is coupled to the sensors 120 of the signaling device 110 and can be programmed to control the sending of an alert through an alert system 850 if the presences of liquid is detected in the pair of training pants 20.

In some embodiments, the capacitive sensor 120 and/or signal device 110 can include multiple settings depending upon the particular pair of training pants 20 to which it is attached. In this manner, the signaling system can be modified based upon the particular product specifications. In some embodiments, the signal device 110 determines the particular product to which it is attached by detecting the electrical properties of the conductive pattern 201 on the pair of training pants as described above. In such embodiments, each group of products that utilizes the same setting for signal device 110 includes the same conductive pattern 201 having a particular "electrical fingerprint". Products having different characteristics, and requiring different settings for signaling device 110, will have a different conductive pattern having different electrical fingerprints. Thus, in addition to determining whether it is coupled to an authorized or unauthorized product, the signaling device 110 can also be configured to determine the appropriate settings for a particular product to which it is attached based on the detected conductive pattern of the particular product.

With reference again FIG. 3, the conductive pattern 201 printed on the illustrated pair of training pants 20 can be visible or partially visible from interior of the pair of training pants 20. The term "visible from interior of the pair of training pants" as used herein means visible while looking at the inner surface 28 of the pair of training pants 20 in a direction from the inner surface to the outer surface 30 of the pants. Suitably, however, the conductive pattern 201 is hidden from view such that the conductive pattern is not visible from either interior or exterior the pair of training pants 20.

Figure 5:
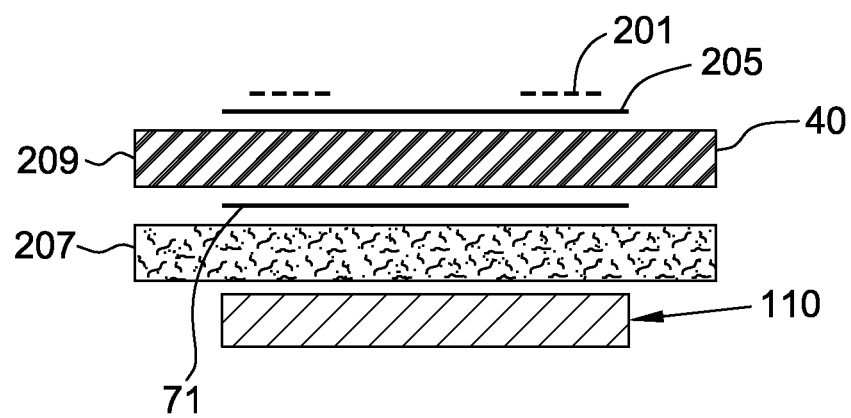
FIG. 5 is an exploded cross section taken along line 5-5 of FIG. 3.

In one suitable embodiment, which is illustrated in FIG. 5, the outer cover 40 comprises a liquid permeable outer layer 207, such as, e.g., a fibrous non-woven web, and a liquid impermeable inner layer 209, such as, e.g., a polymeric film. In the illustrated embodiment, the conductive pattern 201 is printed on the inner surface of inner layer 209 of the outer cover 40 and one or more of the graphic elements 71 are printed on the outer surface of the inner layer of the outer cover. Thus, in the illustrated embodiment, the graphic elements 71 are covered by the outer layer 207 of the outer cover 40. It is understood that the conductive pattern 201 and one or more graphic elements 71 can be printed on different surfaces of the outer cover than those illustrated herein.

For example, in another suitable embodiment, both the conductive pattern 201 and one or more of the graphic elements 71 can be printed on the inner surface of the inner layer 209 of the outer cover. In yet another suitable embodiment, both the conductive pattern 201 and one or more of the graphic elements 71 can be printed on the outer surface of the inner layer 209 of the outer cover. In still another suitable embodiment, the conductive pattern 201 can be printed on either the inner or outer surface of the inner layer 209 and the one or more of the graphic elements 71 can be printed on either the inner or outer surface of the outer layer 207 of the outer cover 40. In yet still another suitable embodiment, both the conductive pattern 201 and the graphic elements 71 can be printed on the same surface (i.e., either the inner surface or the outer surface) of the outer layer 207 of the outer cover 40. In yet a further suitable embodiment, one or more of the graphic elements 71 can be printed on the outer surface of the outer layer 207 of the outer cover 40 and the conductive pattern 201 can be printed on the inner surface of the outer layer.

With reference still to FIG. 5, the conductive pattern 201 is at least partially superposed with one or more of the graphic elements 71. The term "superposed" as used in reference to the conductive pattern 201 and the graphic element 71 is intended to refer to the relative longitudinal and lateral locations of the conductive pattern and the graphic element irrespective of whether the conductive pattern and the graphic element are in direct overlaid relationship with each other (such as where the conductive pattern and the graphic element are both printed on the inner surface of the inner layer 209 of the outer cover 40), or spaced from each other (such as where the conductive pattern is printed on the inner surface of the inner layer of the outer cover and the graphic element is printed on the outer surface of the inner layer as seen in FIG. 5), or otherwise separated from each other by other components disposed between (in the thickness direction).

In one suitable embodiment, the conductive pattern 201 is formed via printing using carbon black ink. The carbon black ink can be applied to the pair of training pants 20 using any suitable printing process, such as a flexographic printing process. Flexographic printing apparatus and processes are known to those skilled in art and need not be further described herein. For example such apparatus are shown and/or described in U.S. Pat. No. 5,458,590 (Schleinz et al.); U.S. Pat. No. 5,566,616 (Schleinz et al.); U.S. 2003/0019374A1 (Harte); and U.S. Pat. No. 4,896,600 (Rogge et al.). Alternatively, the carbon black ink can be printed, sprayed, or otherwise applied to the training pants 20 by another suitable printing method (e.g., ink jet, rotogravure, etc.) or by combinations thereof.

In one suitable embodiment, the carbon black ink (as printed and dried on the outer cover 40 of the pair of training pants 20) has a capacitance between about 10 picofarads and about 1,000 picofarads and a resistivity between about 0 k Ohms/in$^2$ and about 1,000 k Ohms/in$^2$. For example, in one suitable embodiment, the carbon black ink has a capacitance of about 25 picofarads and/or a resistivity of about 100 k Ohms/in$^2$. The dielectric constant of the carbon black ink (as printed and dried on the outer cover 40 of the pair of training pants 20) is suitably between about 1 and 15. In one suitable embodiment, the carbon black ink has a dielectric constant of about 5.

With reference now to FIGS. 3 and 5, a barrier layer 205 is disclosed between the superposed graphic element 71 and conductive pattern 201 to inhibit the conductive pattern 201 from altering or otherwise minimizing the visual quality of the graphic element. That is, the barrier layer 205 inhibits the conductive pattern 201 from diminishing the visual quality of the graphic element 71 visible exterior the pair of training pants 20. In one suitable embodiment, the barrier layer 205 is formed from a high opacity ink printed onto the outer cover 40 of the pair of training pants 20. Suitably, the opacity of the portion of the outer cover 40 to which the barrier layer 205 is printed is between about 50% and about 100% and more suitably between about 85% and 100%. In one embodiment, the portion of the outer cover 40 to which the barrier layer 205 is printed has an opacity of about 85%. The high opacity ink can be made using materials with high refractive index properties, e.g., titanium dioxide, zinc oxide, zinc sulfide and the like. One suitable high opacity ink for forming the barrier layer 205 is a white ink made by mixing micro titanium dioxide (e.g., Microtitan 100ZR available from TRI-K Industries of Denville, N.J., U.S.A.) and polyurethane (e.g., GIOVAREZ P-0580 available from Phoenix Chemical, Inc. of Somerville, N.J., U.S.A.) in ethanol solvent. In one suitable embodiment, the ink comprises between about 20% by weight and about 70% by weight titanium dioxide and suitably about 45% by weight titanium dioxide. Suitably, the ink will have an add-on amount between about 5 billion cubic microns/square inch (bcm) and about 20 bcm, such as, 10 bcm.

Suitably, the ink used for the barrier layer 205 has a viscosity between about 25 seconds (2 Zahn) and about 50 seconds (2 Zahn) and more suitably about 29 seconds (2 Zahn). The viscosity within this range helps control ink wettability and print speed. In one suitable embodiment, for example, the print speed is between about 800 feet per minute (fpm) and about 2000 fpm, such as, 1200 fpm. In one suitable embodiment, the ink used for the barrier layer 205 can be dried at a temperature between about 155 degrees F. and about 210 degrees F. For example, in one embodiment, the ink can be dried at a temperature of about 190 degrees F. Suitably, the dried ink (i.e., barrier layer 205) has color fastness between about 2 (crock rating) and about 5 (crock rating), such as, a crock rating of 4.

The barrier layer 205 can be applied to the pair of training pants 20 using any suitable printing process, such as a flexographic printing process. Flexographic printing apparatus and processes are known to those skilled in art and need not be further described herein. For example such apparatus are shown and/or described in U.S. Pat. No. 5,458,590 (Schleinz et al.); U.S. Pat. No. 5,566,616 (Schleinz et al.); U.S. 2003/0019374A1 (Harte); and U.S. Pat. No. 4,896,600 (Rogge et al.). Alternatively, the barrier layer 205 can be printed, sprayed, or otherwise applied to the training pants 20 by another suitable printing method (e.g., ink jet, rotogravure, etc.) or by combinations thereof.

Suitably, as seen in FIG. 3, the barrier layer 205 covers a larger surface area than the conductive pattern 201 such that the barrier layer underlies the entire conductive pattern. In one suitable embodiment, for example, the barrier layer 205 covers a surface area of approximately 6.5 cm$^2$ and the conductive pattern 201 covers a surface area of approximately 4.1 cm$^2$. Accordingly, no portion of the conductive pattern 201 extends beyond the barrier layer 205. It is understood that the conductive pattern 201 and/or the barrier layer 205 can have surface areas different surface areas than those provided above.

As illustrated in FIG. 3, the barrier layer 205 has a length L1 and a width W1 that are greater than the length L2 and width W2, respectively, of the conductive pattern. In one suitable embodiment, the conductive pattern 201 is at least 5 mm from the periphery edge of the barrier layer 205. In such an embodiment, the length L1 of the barrier layer 205 would be at least 5 mm greater than the length L2 of the conductive pattern 201, and the width W1 of the barrier layer would be at least 5 mm greater than the width W2 of the conductive pattern. It is understood that the barrier layer 205 and/or the conductive pattern 201 can have lengths and width different than those provided herein.

In the embodiment illustrated in FIGS. 3 and 5, the conductive pattern 201 is printed directly to the barrier layer 205. More specifically, in the illustrated embodiment, the barrier layer 205 is printed on the inner surface of the inner layer 209 of the outer cover 40 and then after the barrier layer has sufficiently dried the conductive pattern 201 is printed on the barrier layer. It is understood, however, that in other embodiments the barrier layer 205 and the conductive pattern 201 can be in spaced relationship. For example, the barrier layer 205 can be printed beneath the graphic element 71 on the outer surface of the inner layer 209 of the outer cover.

In another suitable embodiment, the conductive pattern 201, one or more of the graphic elements 71, and the barrier layer 205 can be printed on the inner surface of the inner layer 209 of the outer cover so long as the barrier layer is disposed between the conductive pattern and the one or more graphic elements. In yet another suitable embodiment, the conductive pattern 201, one or more of the graphic elements 71, and the barrier layer 205 can be printed on the outer surface of the inner layer 209 of the outer cover so long as the barrier layer is disposed between the conductive pattern and the one or more graphic elements.

In still another suitable embodiment, the conductive pattern 201 and barrier layer 205 can be printed on either the inner or outer surface of the inner layer 209 and the one or more of the graphic elements 71 can be printed on either the inner or outer surface of the outer layer 207 of the outer cover 40. In still yet another suitable embodiment, the conductive pattern 201 can be printed on either the inner or outer surface of the inner layer 209 and the one or more of the graphic elements 71 and barrier layer 205 can be printed on either the inner or outer surface of the outer layer 207 of the outer cover 40.

In yet still another suitable embodiment, both the conductive pattern 201, the barrier layer 205, the graphic elements 71 can be printed on the same surface (i.e., either the inner surface or the outer surface) of the outer layer 207 of the outer cover 40. In yet a further suitable embodiment, one or more of the graphic elements 71 can be printed on the outer surface of the outer layer 207 of the outer cover 40 and the conductive pattern 201 can be printed on the inner surface of the outer layer. In such an embodiment, the barrier layer 205 can be printed on either the outer surface of the outer layer 207 or the inner surface of the outer layer so long as the barrier layer is disposed between the graphic element(s) 71 and the conductive pattern.

In still further embodiments, the conductive pattern 201, barrier layer 205 and one or more graphic elements 71 can be printed on separate surfaces of the outer cover 40. For example, the conductive pattern 201 can be printed on the inner surface of the inner layer 209 of the outer cover 40, the barrier layer 205 can be printed on the outer surface of the inner layer and the one or more graphic elements 71 can be printed on the either surface of the outer layer 207 of the outer cover.

In one suitable embodiment, the inner layer 209 and the outer layer 207 of the outer cover 40 are either relatively transparent or translucent. In another suitable embodiment, the inner layer 209 of the outer cover 40 can be opaque. In such an embodiment, the inner layer 209 can be the barrier layer 205. For example, the conductive pattern 201 can be printed on the inner surface of the opaque inner layer 209 of the outer cover 40 and the one or more graphic elements 71 can be printed on the outer surface of the inner layer or the inner or outer surfaces of the outer layer 207. The opaque inner layer 209 inhibits the conductive pattern 201 from potentially diminishing the visual quality of the one or more graphic elements 71 visible exterior the pair of training pants.

With reference now to FIGS. 3 and 5, the outer cover 40 can be elastic, stretchable or non-stretchable and, as described above, is desirably a multi-layered laminate structure of which at least one of the layers is liquid impermeable. It is understood, however, that the outer cover 40 may instead be constructed of a single layer of impermeable material. The liquid permeable outer layer 207 of the outer cover 40 can be any suitable material and is desirably one that provides a generally cloth-like texture. One example of such a material is a 20 gsm (grams per square meter) spunbond polypropylene non-woven web.

The liquid impermeable inner layer 209 of the outer cover 40 can be either vapor permeable (i.e., "breathable") or vapor impermeable. The inner layer 209 is desirably manufactured from a thin plastic film, although other flexible liquid impermeable materials may also be used. The liquid impermeable inner layer 209 (or the liquid impermeable outer cover 40 where the outer cover is of a single-layer construction) inhibits liquid body waste from leaking out of the pair of training pants 20 and wetting articles, such as bed sheets and clothing, as well as the wearer and/or care giver. One suitable liquid impermeable material for such use is a 0.02 millimeter polyethylene film commercially available from Huntsman Packaging of Newport News, Va., U.S.A.

As previously mentioned, the liquid impermeable inner layer 209 of the outer cover 40 can permit vapors to escape from the pair of training pants 20 while preventing liquids from passing therethrough. A suitable liquid impermeable, vapor permeable material is composed of a microporous polymer film or a non-woven fabric which has been coated or otherwise treated to impart a desired level of liquid impermeability. A suitable microporous film is a PMP-1 film material commercially available from Mitsui Toatsu Chemicals, Inc., Tokyo, Japan, or an XKO-8044 polyolefin film commercially available from 3M Company, Minneapolis, Minn., U.S.A.

These and other modifications and variations to the present disclosure can be practiced by those of ordinary skill in the art, without departing from the spirit and scope of the present disclosure, which is more particularly set forth in the appended claims. In addition, it should be understood that aspects of the various aspects can be interchanged both in whole and in part. Furthermore, those of ordinary skill in the art will appreciate that the foregoing description is by way of example only, and is not intended to limit the disclosure so further described in such appended claims.

As various changes could be made in the above constructions and methods, without departing from the scope of the invention, it is intended that all matter contained in the above description and shown in the accompanying drawings shall be interpreted as illustrative and not in a limiting sense.

When introducing elements of the invention or the preferred aspect(s) thereof, the articles "a", "an", "the" and "said" are intended to mean that there are one or more of the elements. The terms "comprising", "including" and "having" are intended to be inclusive and mean that there may be additional elements other than the listed elements.

What is claimed is:

1. A liquid detection system comprising:
    an absorbent article for personal wear comprising:
        a liquid permeable liner defining an interior of the absorbent article;
        an outer cover defining an exterior of the absorbent article;
        an absorbent body disposed between the liner and the outer cover; and
        at least one graphic element, a conductive pattern at least partially superposed with the graphic element, and a barrier layer disposed between the graphic element and the conductive pattern, wherein the barrier layer is formed by spraying or printing a white ink comprising titanium dioxide to the outer cover and wherein no portion of the conductive pattern extends beyond a periphery edge of the barrier layer; and
    a non-invasive signaling device selectively attachable to the outer cover of the absorbent article in overlying relationship with the conductive pattern, the signaling device being adapted to detect the presence of liquid within the absorbent article.

2. The liquid detection system set forth in claim 1 wherein the barrier layer is located on a portion of the outer cover, the portion of the outer cover having an opacity between 50% and 100%.

3. The liquid detection system set forth in claim 2 wherein the opacity of the outer cover is about 85%.

4. The liquid detection system set forth in claim 1 wherein the barrier layer covers a larger surface area than the conductive pattern such that the barrier layer underlies the entire conductive pattern.

5. The liquid detection system set forth in claim 1 wherein each of the at least one graphic element, the conductive pattern, and the barrier layer are located on an outer surface of the outer cover.

6. An absorbent article for use with a non-invasive signaling device, the absorbent article comprising:
    a liquid permeable liner defining an interior of the absorbent article;
    an outer cover defining an exterior of the absorbent article;
    an absorbent body disposed between the liner and the outer cover;
    at least one graphic element;
    a conductive pattern at least partially superposed with the graphic element; and
    a barrier layer disposed between the graphic element and the conductive pattern, wherein the barrier layer is formed by spraying or printing a white ink comprising titanium dioxide to the outer cover and wherein no portion of the conductive pattern extends beyond a periphery edge of the barrier layer.

7. The absorbent article set forth in claim 6 wherein the conductive pattern has an electrical fingerprint based on at least one of conductivity, capacitance, and inductance of the conductive pattern.

8. The absorbent article set forth in claim 6 wherein the conductive pattern is formed by applying carbon black ink to the outer cover.

9. The absorbent article set forth in claim 6 wherein conductive pattern has a capacitance between 10 picofarads and 1,000 picofarads.

10. The absorbent article set forth in claim 6 wherein the barrier layer is located on a portion of the outer cover, the portion of the outer cover having an opacity between 50% and 100%.

11. The absorbent article set forth in claim 6 wherein the conductive pattern has a dielectric constant between 1 and 15.

12. An outer cover for an absorbent article, the outer cover comprising at least one graphic element, a conductive pattern at least partially superposed with the graphic element, and a barrier layer disposed between the graphic element and the conductive pattern, wherein the barrier layer is formed by spraying or printing a white ink comprising titanium dioxide to the outer cover and wherein no portion of the conductive pattern extends beyond a periphery edge of the barrier layer.

13. The outer cover set forth in claim 12 wherein the outer cover comprises a laminate having an inner layer and an outer layer.

14. The outer cover set forth in claim 13 wherein the graphic element is disposed on an outer surface of the inner layer, and the conductive pattern is disposed on the inner surface of the inner layer.

15. The outer cover set forth in claim 14 wherein the barrier layer is disposed on the inner surface of the inner layer.

16. The outer cover set forth in claim 15 wherein the conductive pattern is formed by printing the conductive pattern onto the barrier layer.

17. The outer cover set forth in claim 16 wherein a portion of the outer cover including the barrier layer has an opacity between 50% and 100%.

* * * * *